United States Patent [19]

Treuner et al.

[11] Patent Number: 4,534,896
[45] Date of Patent: Aug. 13, 1985

[54] 3-ACYLAMINO-2-OXOAZETIDINE-1-($\beta$-OXOPROPIONIC ACID)

[75] Inventors: Uwe D. Treuner, Regensburg; Hermann Breuer, Schoenhofen, both of Fed. Rep. of Germany

[73] Assignee: E. R. Squibb & Sons, Inc., Princeton, N.J.

[21] Appl. No.: 503,964

[22] Filed: Jun. 13, 1983

[51] Int. Cl.³ ............... C07D 205/08; A61K 31/395; A61K 403/12; A61K 401/12
[52] U.S. Cl. .................. 260/239 A; 260/245.4; 260/330.3; 260/330.9; 260/239.3 R; 544/238; 544/279; 544/327; 544/335; 544/336; 544/359; 544/182; 544/215; 546/275; 546/208; 514/210
[58] Field of Search ............ 260/245.4, 239 A, 330.3, 260/330.9, 239.3 R; 544/182, 215, 279, 327, 335, 336, 359; 546/208, 275

[56] References Cited

FOREIGN PATENT DOCUMENTS 85291 8/1983 European Pat. Off. .

*Primary Examiner*—Mark L. Berch
*Attorney, Agent, or Firm*—Lawrence S. Levinson; Donald J. Barrack

[57] ABSTRACT

Antibacterial activity and $\beta$-lactamase inhibitory activity is exhibited by $\beta$-lactams having a 3-acylamino substituent and in the 1-position a group having the formula

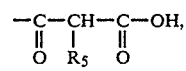

wherein $R_5$ is hydrogen, methyl or ethyl.

12 Claims, No Drawings

3-ACYLAMINO-2-OXOAZETIDINE-1-(β-OXOPROPIONIC ACID)

BRIEF DESCRIPTION OF THE INVENTION

Antibacterial and β-lactamase inhibitory activity is exhibited by β-lactams having the formula

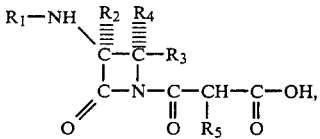

and salts and hydrolyzable esters thereof. In formula I, and throughout the specification, the symbols are as defined below:

$R_1$ is acyl;

$R_2$ is hydrogen or methoxy;

$R_3$ and $R_4$ are the same or different and each is hydrogen, alkyl, alkenyl, alkynyl, cycloalkyl, phenyl, substituted phenyl or a 4,5,6 or 7-membered heterocycle (referred to hereinafter as $R_6$) or one of $R_3$ and $R_4$ is hydrogen and the other is azido, halomethyl, dihalomethyl, trihalomethyl, alkoxycarbonyl, alkenyl, alkynyl, 2-phenylethenyl, 2-phenylethynyl, carboxyl, —$CH_2X_1$ [wherein $X_1$ is azido, amino (—$NH_2$), hydroxy, alkanoylamino, alkylsulfonyloxy, phenylsulfonyloxy, (substituted phenyl)sulfonyloxy, phenyl, substituted phenyl, cyano,

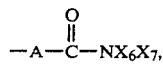

—S—$X_2$, or —O—$X_2$ (wherein A, $X_2$, $X_6$ and $X_7$ are as hereinafter defined)], —S—$X_2$ or —O—$X_2$ [wherein $X_2$ is alkyl, substituted alkyl, phenyl, substituted phenyl, phenylalkyl, (substituted phenyl)alkyl, alkanoyl, phenylalkanoyl, substituted alkanoyl, phenylcarbonyl, (substituted phenyl)carbonyl, or heteroarylcarbonyl].

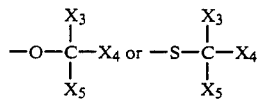

[wherein one of $X_3$ and $X_4$ is hydrogen and the other is hydrogen or alkyl, or $X_3$ and $X_4$ when taken together with the carbon atom to which they are attached form a cycloalkyl group; and $X_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl

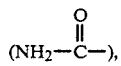

(substituted amino) carbonyl, or cyano (—C≡N)], or

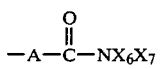

wherein A is —CH=CH—, —(CH$_2$)$_n$—, —CH$_2$—O—, —CH$_2$—NH—, or —CH$_2$—S—CH$_2$—, n is 0, 1 or 2, and $X_6$ and $X_7$ are the same or different and each is hydrogen or alkyl, or $X_6$ is hydrogen and $X_7$ is amino, substituted amino, acylamino or alkoxy); and $R_5$ is hydrogen, or alkyl of 1 to 4 carbon atoms.

Listed below are definitions of various terms used to describe the β-lactams of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The terms "cycloalkyl" and "cycloalkenyl" refer to cycloalkyl and cycloalkenyl groups having 3,4,5,6 or 7 carbon atoms.

The term "substituted alkyl" refers to alkyl groups substituted with one, or more, azido, amino (—$NH_2$), halogen, hydroxy, carboxy, cyano, alkoxycarbonyl, aminocarbonyl, alkanoyloxy, alkoxy, phenyloxy, (substituted phenyl)oxy, $R_6$-oxy, mercapto, alkylthio, phenylthio, (substituted phenyl)thio, alkylsulfinyl, or alkylsulfonyl groups.

The terms "alkanoyl", "alkenyl", and "alkynyl" refer to both straight and branched chain groups. Those groups having 2 to 10 carbon atoms are preferred.

The terms "halogen" and "halo" refer to fluorine, chlorine, bromine and iodine.

The term "protected carboxyl" refers to a carboxyl group which has been esterified with a conventional acid protecting group. These groups are well known in the art; see, for example, U.S. Pat. No. 4,144,333, issued Mar. 13, 1979. The preferred protected carboxyl groups are benzyl, benzhydryl, t-butyl, and p-nitrobenzyl esters.

The term "substituted phenyl" refers to a phenyl group substituted with 1, 2 or 3 amino (—$NH_2$), halogen, hydroxyl, trifluoromethyl, alkyl (of 1 to 4 carbon atoms), alkoxy (of 1 to 4 carbon atoms), or carboxyl groups.

The expression "a 4,5,6 or 7-membered heterocycle" (referred to as "$R_6$") refers to substituted and unsubstituted, aromatic and non-aromatic groups containing one or more nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, and substituted alkyl groups (wherein the alkyl group has 1 to 4 carbons). One type of "4,5,6 or 7-membered heterocycle" is the "heteroaryl" group. The term "heteroaryl" refers to those 4,5,6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4,5,6 or 7-membered heterocycles are 1-alkyl-3-azetinyl, 2-oxo-1-imidazolidinyl, 3-alkylsulfonyl-2-oxo-1-imidazolidinyl, 3-benzylimino-2-oxo-1-imidazolidinyl, 3-alkyl-2-oxo-1-imidazolidinyl, 3-phenyl (or substituted phenyl)-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxy-carbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-furanyl, 2,3-dioxo-1-piperazinyl, 2,5-dioxo-1-piperazinyl, 4-alkyl-2,3-dioxo-1-piperazinyl, and 4-phenyl-2,3-dioxo-1-piperazinyl.

The term "substituted amino" refers to a group having the formula —NH$_1$Y$_2$ wherein Y$_1$ is hydrogen, alkyl, phenyl, substituted phenyl, phenylalkyl or (substituted phenyl)alkyl, and Y$_2$ is alkyl, phenyl, substituted phenyl, phenylalkyl, (substituted phenyl)alkyl, hydroxy, cyano, alkoxy, phenylalkoxy, or amino (—NH$_2$).

The term "acyl" refers to all organic radicals derived from an organic acid (i.e., a carboxylic acid) by removal of the hydroxyl group. Certain acyl groups are, of course, preferred but this preference should not be viewed as a limitation of the scope of this invention. Exemplary acyl groups are those acyl groups which have been used in the past to acylate β-lactam antibiotics including 6-aminopenicillanic acid and derivatives and 7-aminocephalosporanic acid and derivatives; see, for example, *Cephalosporins and Penicillins*, edited by Flynn, Academic Press (1972), German Offenlegungsschrift No. 2,716,677, published Oct. 10, 1978, Belgian Pat. No. 867,994, published Dec. 11, 1978, U.S. Pat. No. 4,152,432, issued May 1, 1979, U.S. Pat. No. 3,971,778, issued July 27, 1976, U.S. Pat. No. 4,172,199, issued Oct. 23, 1979, and British Pat. No. 1,348,894, published Mar. 27, 1974. The portions of these references describing various acyl groups are incorporated herein by reference. The following list of acyl groups is presented to further exemplify the term "acyl"; it should not be regarded as limiting that term. Exemplary acyl groups are:

(a) Aliphatic groups having the formula

wherein R$_a$ is alkyl; cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Carbocyclic aromatic groups having the formula

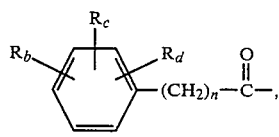

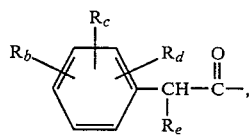

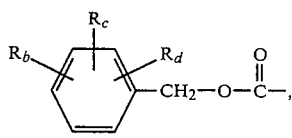

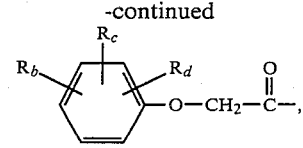

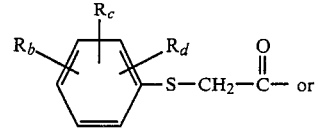

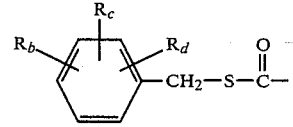

wherein n is 0, 1, 2 or 3; R$_b$, R$_c$, and R$_d$ each is independently hydrogen, halogen, hydroxyl, nitro, amino, cyano, trifluoromethyl, alkyl of 1 to 4 carbon atoms, alkoxy of 1 to 4 carbon atoms or aminomethyl; and R$_e$ is amino, hydroxyl, a carboxyl salt, protected carboxyl, formyloxy, a sulfo salt, a sulfoamino salt, azido, halogen, hydrazino, alkylhydrazino, phenylhydrazino, or [(alkylthio)thioxomethyl]thio.

Preferred carbocyclic aromatic acyl groups include those having the formula

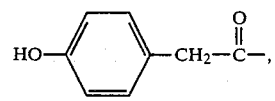

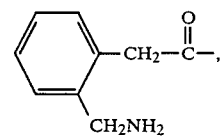

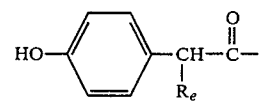

(R$_e$ is preferably a carboxyl salt or sulfo salt) and

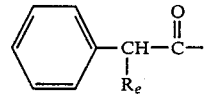

(R$_e$ is preferably a carboxyl salt or sulfo salt).

(c) Heteroaromatic groups having the formula

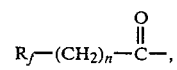

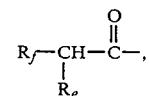

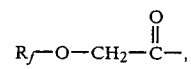

$$R_f-S-CH_2-\overset{\overset{O}{\|}}{C}-,$$

$$R_f-\overset{\overset{O}{\|}}{C}-\overset{\overset{O}{\|}}{C}-,$$

wherein n is 0, 1, 2 or 3; $R_e$ is as defined above; and $R_f$ is a substituted or unsubstituted 5-, 6- or 7-membered heterocyclic ring containing 1,2,3 or 4 (preferably 1 or 2) nitrogen, oxygen and sulfur atoms. Exemplary heterocyclic rings are thienyl, furyl, pyrrolyl, pyridinyl, pyrazolyl, pyrazinyl, thiazolyl, pyrimidinyl, thiadiazolyl and tetrazolyl. Exemplary substituents are halogen, hydroxyl, nitro, amino, protected amino, cyano, trifluoromethyl, alkyl of 1 to 4 carbon atoms, alkoxy of 1 to 4 carbon atoms, or $$HOOC-\underset{\underset{NH_2}{|}}{CH}-CH_2-O-\overset{\overset{O}{\|}}{C}-NH-.$$

Preferred heteroaromatic acyl groups include those groups of the above formulas wherein $R_f$ is 2-amino-4-thiazolyl, 2-amino-5-halo-4-thiazolyl, 4-aminopyrimidin-2-yl, 5-amino-1,2,4-thiadiazol-3-yl, 2-thienyl, 2-furanyl, or 6-aminopyridin-2-yl.

(d) [[(4-Substituted-2,3-dioxo-1-piperazinyl)carbonyl]amino]arylacetyl groups having the formula <chemical structure: -C(=O)-CH(Rg)-NH-C(=O)-N(piperazine-2,3-dione)-N-Rh> wherein $R_g$ is an aromatic group (including carbocyclic aromatics such as those of the formula <chemical structure: phenyl ring with Rb, Rc, Rd substituents> and heteroaromatics as included within the definition of $R_f$); and $R_h$ is alkyl, substituted alkyl (wherein the alkyl group is substituted with one or more halogen, cyano, nitro, amino or mercapto groups), arylmethyleneamino (i.e., —N=CH—$R_g$ wherein $R_g$ is as defined above), arylcarbonylamino $$-NH-\overset{\overset{O}{\|}}{C}-R_g$$

wherein $R_g$ is as defined above) or alkylcarbonylamino.

Preferred [[(4-substituted-2,3-dioxo-1-piperazinyl)carbonyl]amino]arylacetyl groups include those wherein $R_h$ is ethyl, phenylmethyleneamino or 2-furylmethyleneamino.

(e) (Substituted oxyimino)arylacetyl groups having the formula $$-\overset{\overset{O}{\|}}{C}-\underset{\underset{R_g}{|}}{C}=N-O-R_i$$

wherein $R_g$ is as defined above and $R_i$ is hydrogen, alkyl, cycloalkyl, alkylaminocarbonyl, arylaminocarbonyl (i.e., $$-\overset{\overset{O}{\|}}{C}-NH-R_g$$

wherein $R_g$ is as defined above) or substituted alkyl (wherein the alkyl group is substituted with one or more halogen, cyano, nitro, amino, mercapto, alkylthio, aromatic group (as defined by $R_g$), carboxyl (including salts thereof), amido, alkoxycarbonyl, phenylmethoxycarbonyl, diphenylmethoxycarbonyl, hydroxyalkoxyphosphinyl, dihydroxyphosphinyl, hydroxy(phenylmethoxy)phosphinyl, or dialkoxyphosphinyl substituents).

Preferred (substituted oxyimino)arylacetyl groups include those wherein $R_g$ is 2-amino-4-thiazolyl. Also preferred are those groups wherein $R_i$ is methyl, ethyl, carboxymethyl, 1-carboxy-1-methylethyl, 2,2,2-trifluoroethyl or 1-carboxycyclopropyl.

(f) (Acylamino)arylacetyl groups having the formula $$-\overset{\overset{O}{\|}}{C}-\underset{\underset{R_g}{|}}{CH}-NH-\overset{\overset{O}{\|}}{C}-R_j$$

wherein $R_g$ is as defined above and $R_j$ is

<chemical structure: phenyl ring with Rb, Rc, Rd substituents and -(CH2)n-O-> amino, alkylamino, (cyanoalkyl)-amino, amido, alkylamido, (cyanoalkyl)amido,

<chemical structures showing: -CH2-NH-C(=NH)-pyridinyl;  -CH(NH2)-CH2-C(=O)-NH-CH3; pyridinyl-phenyl-SO2-N(CH2-CH2-OH)2; hydroxypyridinyl-CH3; hydroxynaphthyridinyl>

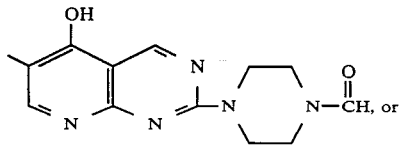

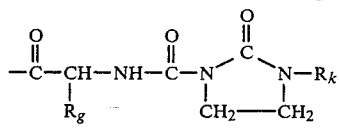

Preferred (acylamino)arylacetyl groups of the above formula include those groups wherein $R_j$ is amino or amido. Also preferred are those groups wherein $R_g$ is phenyl or 2-thienyl.

(g) [[[3-Substituted-2-oxo-1-imidazolidinyl]carbonyl]amino]arylacetyl groups having the formula

wherein $R_g$ is as defined above and $R_k$ is hydrogen, alkylsulfonyl, arylmethyleneamino (i.e., $-N=CH-R_g$ wherein $R_g$ is as defined above), $$-\overset{O}{\underset{\|}{C}}-R_m$$

(wherein $R_m$ is hydrogen, alkyl or halogen substituted alkyl), aromatic group (as defined by $R_g$ above), alkyl or substituted alkyl (wherein the alkyl group is substituted with one or more halogen, cyano, nitro, amino or mercapto groups).

Preferred [[3-substituted-2-oxo-1-imidazolidinyl]carbonyl]amino]arylacetyl groups of the above formula include those wherein $R_g$ is phenyl or 2-thienyl. Also preferred are those groups wherein $R_k$ is hydrogen, methylsulfonyl, phenylmethyleneamino or 2-furylmethyleneamino.

The terms "salt" and "salts" refer to basic salts formed with inorganic and organic bases. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, pharmaceutically acceptable salts are preferred, although other salts are also useful, e.g., in isolating or purifying the product.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin like Dowex 50) or with an aqueous acid and extraction with an organic solvent, e.g., ethyl acetate, dichloromethane or the like, the free acid form can be obtained, and, if desired, another salt formed.

The expression "hydrolyzable ester" refers to any ester group that can be hydrolyzed in vivo to give the parent carboxylic acid product. Exemplary esters include alkyl, phenyl, substituted phenyl, phenylalkyl, (substituted phenyl)alkyl,

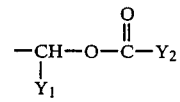

[wherein $Y_1$ is hydrogen, alkyl or phenyl and $Y_2$ is hydrogen, alkyl, phenyl, or alkoxy, or together $Y_1$ and $Y_2$ are $-(CH_2)_2-$, $-(CH_2)_3-$, $-CH=CH-$, or

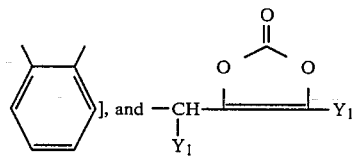

β-Lactams having a

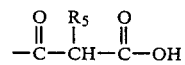

substituent (or a hydrolyzable ester or salt thereof) in the 1-position and an amino or acylamino substituent in the 3-position contain at least one chiral center—the carbon atom (in the 3-position of the β-lactam nucleus) to which the amino or acylamino substituent is attached. This invention is directed to those β-lactams which have been described above, wherein the stereochemistry at the chiral center in the 3-position of the β-lactam nucleus is the same as the configuration at the carbon atom in the 6-position of naturally occurring penicillins (e.g., penicillin G) and as the configuration at the carbon atom in the 7-position of naturally occurring cephamycins, (e.g., cephamycin C).

Also included within the scope of this invention are racemic mixtures which contain the above-described β-lactams.

DETAILED DESCRIPTION OF THE INVENTION

The compounds of formula I (and salts and hydrolyzable esters thereof) can be used as agents to combat bacterial infections (including urinary tract infections and respiratory infections) in mammalian species, such as domesticated animals (e.g., dogs, cats, cows, horses, and the like) and humans.

For combating bacterial infections in mammals, a compound of this invention can be administered to a mammal in need thereof in an amount of about 1.4 mg/kg/day to about 350 mg/kg/day, preferably about 14 mg/kg/day to about 100 mg/kg/day. All modes of administration which have been used in the past to deliver penicillins and cephalosporins to the site of the infection are also contemplated for use with the novel family of β-lactams of this invention. Such methods of administration include oral, intravenous, intramuscular, and as a suppository.

The compounds of formula I (and salts and hydrolyzable esters thereof) can also be used to inhibit the activity of β-lactamase enzymes. They can be used to protect substances which are inactivated by β-lactamases from degradation by these enzymes and to enhance the antibacterial activity of antibiotics which are affected by β-lactamases.

The β-lactams of this invention can be prepared from a compound having the formula

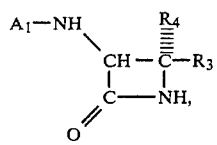

wherein $A_1$ is a nitrogen protecting group, e.g., benzyloxycarbonyl, t-butoxycarbonyl, and triphenylmethyl. Introduction of the 1-activating group can be accomplished by first silylating a compound of formula II using, for example, monosilyltrifluoroacetamide, trimethylsilylchloride/triethylamine, bis-trimethylsilyltrifluoroacetamide, or N-methyl-N-trimethylsilyltrifluoroacetamide.

The resulting 1-silylated derivative can be reacted with a compound having the formula

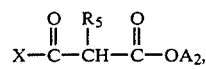

wherein X is a leaving group such as a halogen, methanesulfonyl or toluenesulfonyl group, and $A_2$ is a carboxyl protecting group, to yield a compound having the formula

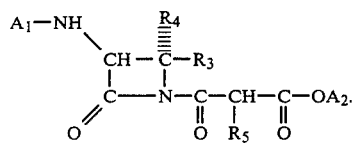

The protecting groups $A_1$ and $A_2$ should be chosen so that it is possible to remove the $A_1$ group, leaving the $A_2$ group in place, yielding a compound having the formula

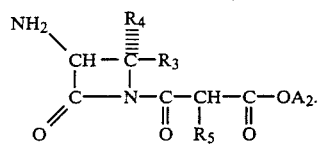

The deprotection techniques used are conventional, and will depend on the particular protecting group ($A_1$) present. Treatment with acid (e.g., formic acid or trifluoroacetic acid) cleaves a triphenylmethyl or a t-butoxycarbonyl protecting group. A benzyloxycarbonylamino protecting group can be cleaved by treatment with trimethylsilyl iodide. Treatment with phosgene or phosphorous pentachloride cleaves an amide protecting group. The compounds of formula V are novel intermediates, and as such, constitute an integral part of this invention.

Conventional acylation techniques can be used to prepare the products of formula I (wherein $R_2$ is hydrogen) from a compound of formula V. Exemplary acylation techniques include reaction with a carboxylic acid ($R_1$—OH), or corresponding carboxylic acid halide or carboxylic acid anhydride. The reaction with a carboxylic acid proceeds most readily in the presence of a carbodiimide and a substance capable of forming an active ester in situ such as N-hydroxybenzotriazole. In those instances wherein the acyl group ($R_1$) contains reactive functionality (such as amino or carboxyl groups) it may be necessary to first protect those functional groups, then carry out the acylation reaction, and finally deprotect the resulting product. The resulting compound has the formula

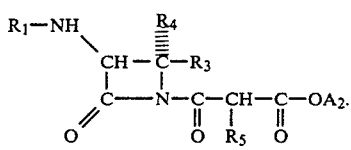

Deprotection of the carboxylic acid group of a compound of formula VI, followed by esterification (if desired), yields the desired product of formula I wherein $R_2$ is hydrogen. It is also possible to prepare those products of this invention which are esters of a compound of formula I by utilizing the desired ester group as the protecting group $A_2$.

Alternatively, the compounds of this invention can be prepared by first silylating a compound of formula II, as described above, and then reacting the 1-silylated compound with a compound having the formula

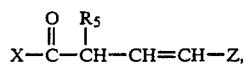

wherein X is a leaving group as defined above and Z is alkyl or aryl, to yield a compound having the formula

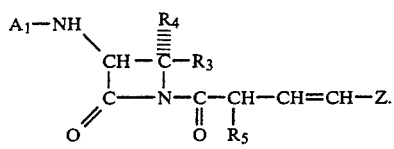

Ozonation of a compound of formula VIII yields the corresponding aldehyde having the formula

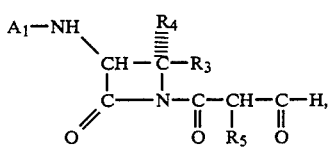

which can be oxidized to yield the corresponding acid having the formula

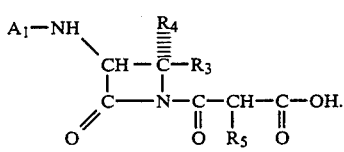

Deprotection of a compound of formula X followed by acylation yields the corresponding compound of formula I. Deprotection and acylation techniques are described above.

Still another method for preparing the compounds of this invention comprises reacting a compound of formula II with a Grignard reagent and then reacting the resulting intermediate with a compound of formula III to give the corresponding compound of formula IV. This can be converted to a product of formula I using the procedure described above.

The β-lactams of formula I wherein R is methoxy can be prepared from the corresponding compound of formula VI. Halogenation of the amide nitrogen of a non-methoxylated compound of formula VI yields, in situ, an intermediate having the formula

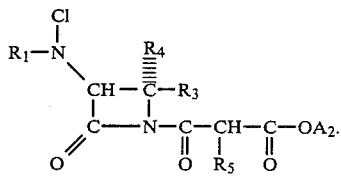   XI

Reaction of an intermediate of formula XI with a methoxylating agent, e.g., an alkali metal methoxide yields a compound having the formula

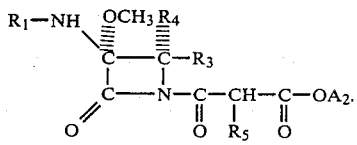   XII

Deprotection of a compound of formula XII yields the corresponding product of formula I wherein $R_2$ is methoxy.

Preferred compounds of this invention are those wherein $R_2$ is hydrogen. Also preferred are those compounds wherein $R_3$ and $R_4$ are the same or different and each is hydrogen or alkyl. The preferred $R_1$ acyl groups are those having the formula:

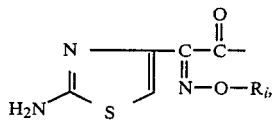

wherein $R_i$ is methyl, ethyl, phenyl, 2,2,2-trifluoroethyl, carboxymethyl, 1-carboxy-1-methylethyl, 1-carboxycyclopentyl, or 1-carboxycyclopropyl.

The following examples are specific embodiments of this invention.

EXAMPLE 1

(S)-β,2-Dioxo-3-[[(phenylmethoxy)carbonyl]amino]-1-azetidinepropionic acid, methyl ester (S)-(2-Oxo-3-azetidinyl)carbamic acid, phenylmethyl ester (4.40 g) and 4 g of N-methyl-N-trimethylsilyltrifluoroacetamide (hereinafter MSTFA) were stirred in 30 ml of acetonitrile (dried over molecular sieves) at a temperature of 60° C. for 2 hours under an argon atmosphere. Acetonitrile was distilled off in vacuo (together with excess MSTFA and trifluoroacetamide that had formed). To the oily residue was added 0.02 millimoles of β-chloro-β-oxopropionic acid, methyl ester. The mixture was maintained for 2 hours at 45° C. under argon. Trimethylsilylchloride that formed was evaporated and the oily residue was chromatographed on silica gel (eluting with dichloromethane/ethyl acetate (9:1) yielding 3.1 g of the title compound as an oil which crystallized after 2 days, melting point 114°–116° C.

IR (film): 1798 cm$^{-1}$ (β-lactam CO); 1750 cm$^{-1}$; 1730 cm$^{-1}$; $^1$H-NMR (DMSOd$_6$: 90 MHz): δ=3.62 (s;3H), 3.8 (s;2H); 3.5–3.92 (m, 2H); 4.88 (m, 1H); 5.04 (s; 2H); 7.38 (s; 5H); 8.16 (d, 1H broad) ppm.

EXAMPLE 2

(S)-3-[[(1,1-Dimethylethoxy)carbonyl]amino]-β,2-dioxo-1-azetidinepropionic acid, methyl ester Following the procedure of Example 1, but utilizing (S)-(2-oxo-3-azetidinyl)carbamic acid, 1,1-dimethylethyl ester as the starting compound, yielded the title compound as a crystalline solid.

IR (film): 1795 cm$^{-1}$ (β-lactam CO); 1750 cm$^{-1}$; 1720 cm$^{-1}$; $^1$H-NMR (DMSO-d$_6$; 90 MHz): δ–1.41 (s,9H); 3.8 (s,2H); 3.47–3.9(m, 2H); 3.67 (s; 3H); 4.82 m, (1H broad); 7.74 (d, 1H broad) ppm.

EXAMPLE 3

(3S-trans)-3-[[(1,1-Dimethylethoxy carbonyl]amino]-4-methyl-β,2-dioxo-1-azetidinepropionic acid, methyl ester Following the procedure of Example 1, but utilizing (3S-trans)-3-[[(1,1-dimethylethoxy)carbonyl]amino]-4-methyl-2-azetidinone as the starting compound, yielded the title compound as an oil.

IR (film): 1800 cm$^{-1}$ (β-lactam CO); 1748 cm$^{-1}$; 1725 cm$^{-1}$; $^1$H-NMR (DMSOd$_6$, 90 MHz): δ–1.40 (s, 9H); 1.53 (d, 2H); 3.7 (s, 3H); 3.78 (s, 2H); 4.15 (m, 2H); 5.72 (d, 2H broad) ppm.

EXAMPLE 4

[3S-[3α(Z),4β]]-3-[[(2-Amino-4-thiazolyl)(methoxyimino)acetyl]amino]-4-methyl-β,2-dioxo-1-azetidinepropionic acid, methyl ester (A)

(3S-trans)-3-Amino-4-methyl-β,2-dioxo-1-azetidinepropionic acid, methyl ester (3S-trans)-3-[[(1,1-Dimethylethoxy)carbonyl]amino]-4-methyl-β,2-dioxo-1-azetidinepropionic acid, methyl ester (0.3 g) was dissolved in 10 ml of dichloromethane/trifluoroacetic acid (7:3) and stirred for 15 minutes at −10° C. After evaporation and treatment with ether, 0.31 g of the title compound was obtained as a crystalline material, melting point 75° C. dec.

IR (film): 1803 cm$^{-1}$; 1760 cm$^{-1}$, $^1$H-NMR (DMSO-d$_6$; 90 MHz): δ=1.6 (d, 3H); 3.69 (s, 3H); 3.8 (d, 2H); 4.38 (m, 1H); 4.61 (d, 1H); 7.58 (3H broad) ppm.

(B)

[3S-[3α(Z),4β]]-3-[[(2-Amino-4-thiazolyl)(methoxyimino)acetyl]amino]-4-methyl-β,2-dioxo-1-azetidinepropionic acid, methyl ester (Z)-2-Amino-α-methoxy-4-thiazoleacetic acid (0.4 g), 0.3 g of N-hydroxybenzotriazole and 0.43 g of dicyclohexylcarbodiimide were dissolved in 20 ml of dimethylformamide (dried over molecular sieves) and stirred at 0° C. for 1 hour. (3S-trans)-3-amino-4-methyl-β,2-dioxo-1-azetidinepropionic acid, methyl ester (0.63 g) and 0.4 g of MSTFA were stirred in 10 ml of dimethylformamide (absolute) at room temperature for 30 minutes. The second reaction solution was added to the first and stirring was continued at 0° C. for 12 hours. Isopropanol (2 ml) was added and after 10 minutes the dicyclohexylurea that formed was filtered off. The filtrate was evaporated and the residue dissolved in 50 ml of ethyl acetate, washed with 2% sodium bicarbonate solution and brine. The organic phase was dried over Na₂SO₄ and evaporated yielding 0.4 g of an oily residue. The residue was chromatographed on silica gel (eluting with ethyl acetate) yielding 0.17 g of the title compound as an etherate, melting point 91° C. dec.

IR (KBr): 1800 cm⁻¹; 1755 cm⁻¹ ¹H-NMR (DMSO-d₆; 90 MHz): δ1.5 (d,3H); 3.64 (s, 3H); 3.82 (d, 2H); 3.85 (s, 3H); 4.15 (m,1H); 4.6 (m, 1H); 6.78 (s, 1H); 7.3 (broad 2H); 9.32 (d, 1H broad).

EXAMPLE 5

[3S-[3α(Z),4β]]-3-[[(2-Amino-4-thiazolyl)[(1-carboxy-1-methylethoxy)imino]acetyl]amino]-4-methyl-β,2-dioxo-1-azetidinepropionic acid, methyl ester (A)

[3S-[3α(Z),4β]]-3-[[(2-Amino-4-thiazolyl)[(1-diphenylmethoxycarbonyl-1-methylethoxy)imino]acetyl]amino]-4-methyl-β,2-dioxo-1-azetinepropionic acid Following the procedure of Example 4, but utilizing (Z)-2-amino-α-[(1-diphenylmethoxycarbonyl-1-methylethoxy)imino]-4-thiazoleacetic acid as the starting acid, yields the title compound.

(B)

[3S-[3α(Z),4β]]-3-[[(2-Amino-4-thiazolyl)[(1-carboxy-1-methylethoxy)imino]acetyl]amino]-4-methyl-β,2-dioxo-1-azetidinepropionic acid

[3S-[3α(Z),4β]]-3-[[(2-Amino-4-thiazolyl)[(1-diphenylmethoxycarbonyl-1-methylethoxy)imino]acetyl]amino]-4-methyl-β,2-dioxo-1-azetidinepropionic acid is freeze-dried and suspended in a solution of trifluoroacetic acid and anisole at −10° C. The trifluoroacetic acid is distilled off 10 minutes later at 0° C., and ether and ice-cold water are added and the pH adjusted to 6.5 with sodium bicarbonate. After freeze-drying the aqueous phase, the crude product is chromatographed to yield the title compound.

EXAMPLE 6

(3S-trans)-3-[[(1,1-Dimethylethoxy)carbonyl]amino]-4-methyl-β,2-dioxo-1-azetidinepropionic acid, potassium salt (A)

(3S-trans-[4-Methyl-2-oxo-1-(1-oxo-4-phenyl-3-butenyl)-3-azetidinyl]carbamic acid, 1,1-dimethylethyl ester (3S-trans)-(4-Methyl-2-oxo-3-azetidinyl)carbamic acid, 1,1-dimethylethyl ester (2 g) and 1.01 g of triethylamine were dissolved in 20 ml of dried ethyl acetate. Over a 15 minute period, a solution of 1.1 g of trimethylsilyl chloride in 15 ml of ethyl acetate was added dropwise. After 12 hours stirring at 0° C., the triethylamine hydrochloride that formed was filtered off and the filtrate was evaporated. The only residue was dissolved in 20 ml of dichloromethane, 10 mmol of 4-phenyl-3-butenyl chloride was added, and the solution was stirred for 2 hours. Evaporation yielded an oily esidue which was chromatographed on silica gel (eluting with dichloromethane-ethyl acetate (9:1)) yielding the title compound as a foam.

(B)

(3S-trans)-3-[[(1,1-Dimethylethoxy)carbonyl]amino]-4-methyl-β,2-dioxo-1-azetidinepropionic acid, potassium salt (3S-trans-[4-Methyl-2-oxo-1-(1-oxo-4-phenyl-3-butenyl)-3-azetidinyl]carbamic acid, 1,1-dimethylethyl ester was dissolved in 30 ml of dichloromethane and at −70° C. a stream of ozone/oxygen was bubbled through the solution until starting material disappeared. A solution of 0.75 g of triphenylphosphine was added dropwise and stirring continued for 1 hour. At a temperature of 0° C., a solution of 0.7 g of meta-chloro-perbenzoic acid was added dropwise.

After 2 hours stirring, the solution was evaporated and the oily residue was dissolved in 20 ml of ethyl acetate. Ether (20 ml) was added and the acidic material in the solution was isolated as potassium salts after adding 2-ethylhexanoic acid, potassium salt (the precipitate contained the potassium salts of benzoic acid and of metachlorobenzoic acid). The potassium salt mixture was chromatographed on HP-20 resin using water as eluent, yielding 210 mg of the title compound as a powder; IR (KBr) 1795 cm⁻¹, melting point 187° C. (dec).

What is claimed is:

1. A compound having the formula

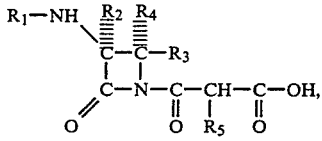

or a pharmaceutically acceptable basic salt or hydrolyzable ester thereof, wherein R₁ is an acyl group derived from a carboxylic acid;
R₂ is hydrogen or methoxy;
R₃ and R₄ are the same or different and each is hydrogen, alkyl, alkenyl, alkynyl, cycloalkyl, phenyl, substituted phenyl or a 4,5,6 or 7-membered heterocycle or one of R₃ and R₄ is hydrogen and the other is azido, halomethyl, dihalomethyl, trihalomethyl, alkoxycarbonyl, alkenyl, alkynyl, 2-phenylethenyl, 2-phenylethynyl, carboxyl, —CH₂X₁, —S—X₂, —O—X₂,

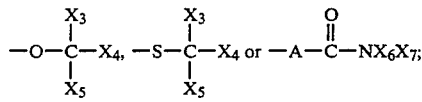

wherein X₁ is azido, amino, hydroxy, alkanoylamino, alkylsulfonyloxy, phenylsulfonyloxy, (substituted phenyl)sulfonyloxy, phenyl, substituted phenyl, cyano,

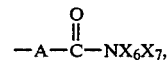

—S—X₂ or —O—X₂; X₂ is alkyl, substituted alkyl, phenyl, substituted phenyl, phenylalkyl, (substituted phenyl)alkyl, alkanoyl, phenylalkanoyl, phenylcarbonyl, (substituted phenyl)carbonyl, or heteroarylcarbonyl; one of X₃ and X₄ is hydrogen and the other is hydrogen or alkyl, or X₃ and X₄ when taken together with the carbon atom to which they are attached form a cycloalkyl group; X₅ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is —CH=CH—, —(CH$_2$)$_n$—, —CH$_2$—O—, —CH$_2$—NH— or —CH$_2$—S—CH$_2$—; n is 0, 1 or 2; and X$_6$ and X$_7$ are the same or different and each is hydrogen or alkyl, or X$_6$ is hydrogen and X$_7$ is amino, substituted amino, or alkoxy); and R$_5$ is hydrogen or alkyl of 1 to 4 carbon atoms;
wherein the terms "alkyl" and "alkoxy" refer to groups having 1 to 10 carbon atoms;
the term "cycloalkyl" refers to groups having 3, 4, 5, 6 or 7 carbon atoms;
the terms "alkanoyl", "alkenyl", and "alkynyl" refer to groups having 2 to 10 carbon atoms;
the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms or carboxyl groups;
the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, (4, 5, 6 or 7-membered heterocycle)oxy, mercapto, alkylthio, phenylthio, (substituted phenyl)thio, alkylsulfinyl or alkylsulfonyl groups;
the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups;
the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups; and
the term "substituted amino" refers to a group having the formula —NY$_1$Y$_2$ wherein Y$_1$ is hydrogen, alkyl, phenyl, substituted phenyl, phenylalkyl or (substituted phenyl)alkyl, and Y$_2$ is alkyl, phenyl, substituted phenyl, phenylalkyl, (substituted phenyl)alkyl, hydroxy, cyano, alkoxy, phenylalkoxy or amino.

2. A compound in accordance with claim 1 wherein R$_2$ is hydrogen.

3. A compound in accordance with claim 1 wherein R$_3$ and R$_4$ are the same or different and each is hydrogen or alkyl.

4. A compound in accordance with claim 1 wherein R$_5$ is hydrogen.

5. A compound in accordance with claim 1 wherein R$_2$ is hydrogen;

R$_3$ and R$_4$ are the same or different and each is hydrogen or alkyl; and
R$_5$ is hydrogen.

6. The compound in accordance with claim 5, (S)-β,2-dioxo-3-[[(phenylmethoxy)carbonyl]amino]-1-azetidinepropionic acid, methyl ester.

7. The compound in accordance with claim 5, (S)-3-[[(1,1-dimethylethoxy)carbonyl]amino]-β,2-dioxo-1-azetidinepropionic acid, methyl ester.

8. The compound in accordance with claim 5, (3S-trans)-3-[[(1,1-dimethylethoxy carbonyl]amino]-4-methyl-β,2-dioxo-1-azetidinepropionic acid, methyl ester.

9. The compound in accordance with claim 5, [3S-[3α(Z),4β]]-3-[[(2-amino-4-thiazolyl)(methoxyimino)acetyl]amino]-4-methyl-β,2-dioxo-1-azetidinepropionic acid, methyl ester.

10. The compound in accordance with claim 5, [3S-[3α(Z),4β]]-3-[[(2-amino-4-thiazolyl)[(1-carboxy-1-methylethoxy)imino]acetyl]amino]-4-methyl-β,2-dioxo-1-azetidinepropionic acid.

11. The compound in accordance with claim 5, (3S-trans)-3-[[(1,1-dimethylethoxy)carbonyl]amino]-4-methyl-β,2-dioxo-1-azetidinepropionic acid, potassium salt.

12. A hydrolyzable ester of a compound having the formula

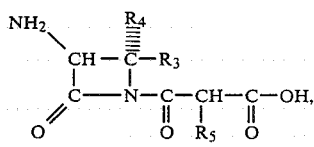

wherein

R$_3$ and R$_4$ are the same or different and each is hydrogen, alkyl, alkenyl, alkynyl, cycloalkyl, phenyl, substituted phenyl or a 4,5,6 or 7-membered heterocycle or one of R$_3$ and R$_4$ is hydrogen and the other is azido, halomethyl, dihalomethyl, trihalomethyl, alkoxycarbonyl, alkenyl, alkynyl, 2-phenylethenyl, 2-phenylethynyl, carboxyl, —CH$_2$X$_1$, —S—X$_2$, —O—X$_2$,

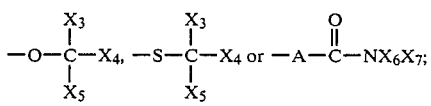

wherein X$_1$ is azido, amino, hydroxy, alkanoylamino, alkylsulfonyloxy, phenylsulfonyloxy, (substituted phenyl)sulfonyloxy, phenyl, substituted phenyl, cyano,

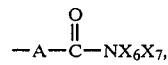

—S—X$_2$ or —O—X$_2$; X$_2$ is alkyl, substituted alkyl, phenyl, substituted phenyl, phenylalkyl, (substituted phenyl)alkyl, alkanoyl, phenylalkanoyl, phenylcarbonyl, (substituted phenyl)carbonyl, or heteroarylcarbonyl; one of X$_3$ and X$_4$ is hydrogen and the other is hydrogen or alkyl, or X$_3$ and X$_4$ when taken together with the carbon atom to which they are attached form a cycloalkyl group; X$_5$ is formyl, alkanoyl, phenylcarbonyl, (substituted phenyl)carbonyl, phenylalkylcarbonyl, (substituted phenyl)alkylcarbonyl, carboxyl, alkoxycarbonyl, aminocarbonyl, (substituted amino)carbonyl, or cyano; A is —CH=CH—, —(CH$_2$)$_n$—, —CH$_2$—O—, —CH$_2$—NH— or —CH$_2$—S—CH$_2$—; n is 0, 1 or 2; and X$_6$ and X$_7$ are the same or different and each is hydrogen or alkyl, or X$_6$ is hydrogen and X$_7$ is amino, substituted amino, or alkoxy); and R$_5$ is hydrogen or alkyl of 1 to 4 carbon atoms;

wherein the terms "alkyl" and "alkoxy" refer to groups having 1 to 10 carbon atoms;

the term "cycloalkyl" refers to groups having 3, 4, 5, 6 or 7 carbon atoms;

the terms "alkanoyl", "alkenyl", and "alkynyl" refer to groups having 2 to 10 carbon atoms;

the term "substituted phenyl" refers to a phenyl group substituted with 1, 2 or 3 amino, halogen, hydroxyl, trifluoromethyl, alkyl of 1 to 4 carbon atoms, alkoxy of 1 to 4 carbon atoms or carboxyl groups;

the term "substituted alkyl" refers to alkyl groups substituted with one or more azido, amino, halogen, hydroxy, carboxy, cyano, alkoxycarbonyl, aminocarbonyl, alkanoyloxy, alkoxy, phenyloxy, (substituted phenyl)oxy, (4, 5, 6 or 7-membered heterocycle)oxy, mercapto, alkylthio, phenylthio, (substituted phenyl)thio, alkylsulfinyl or alkylsulfonyl groups;

the term "heteroaryl" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl or one of the above groups substituted with one or more halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups;

the term "a 4, 5, 6 or 7-membered heterocycle" refers to pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, tetrazolyl, azetinyl, oxetanyl, thietanyl, piperidinyl, piperazinyl, imidazolidinyl, oxazolidinyl, pyrrolidinyl, tetrahydropyrimidinyl, dihydrothiazolyl or hexahydroazepinyl or one of the above groups substituted with one or more oxo, halogen, hydroxy, nitro, amino, cyano, trifluoromethyl, alkyl of 1 to 4 carbon atoms, alkoxy of 1 to 4 carbon atoms, alkylsulfonyl, phenyl, substituted phenyl, or substituted alkyl, wherein the alkyl group has 1 to 4 carbon atoms, groups; and the term "substituted amino" refers to a group having the formula —NY$_1$Y$_2$ wherein Y$_1$ is hydrogen, alkyl, phenyl, substituted phenyl, phenylalkyl or (substituted phenyl)alkyl and Y$_2$ is alkyl, phenyl, substituted phenyl, phenylalkyl, (substituted phenyl)alkyl, hydroxy, cyano, alkoxy, phenylalkoxy or amino.

* * * * *